United States Patent
Kyoung (10) Patent No.: US 10,082,459 B2
(45) Date of Patent: Sep. 25, 2018

(54) METHOD AND APPARATUS FOR MEASURING REFRACTIVE INDEX IN MODEL-FREE MANNER

(71) Applicant: SAMSUNG ELECTRONICS CO., LTD., Suwon-si (KR)

(72) Inventor: Jisoo Kyoung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/491,001

(22) Filed: Apr. 19, 2017

(65) Prior Publication Data

US 2017/0299509 A1   Oct. 19, 2017

(30) Foreign Application Priority Data

Apr. 19, 2016  (KR) .................. 10-2016-0047561

(51) Int. Cl.
*G01N 21/41* (2006.01)

(52) U.S. Cl.
CPC .................. *G01N 21/4133* (2013.01)

(58) Field of Classification Search
CPC ............. G01N 33/487; G01N 21/4133; G01N 21/554; G01N 21/648; G01N 21/658
USPC .................. 356/445–448, 128–137
See application file for complete search history.

(56) References Cited

U.S. PATENT DOCUMENTS

| | | | |
|---|---|---|---|
| 8,048,385 B2 | 11/2011 | Dong et al. | |
| 8,976,360 B2 | 3/2015 | Matsuda et al. | |
| 2009/0225317 A1 | 9/2009 | Tanaka | |
| 2011/0168559 A1* | 7/2011 | Wei | G01N 21/553 204/484 |
| 2012/0032138 A1* | 2/2012 | Kim | H01L 51/502 257/13 |

(Continued)

FOREIGN PATENT DOCUMENTS

| | | |
|---|---|---|
| KR | 10-2004-0094582 A | 11/2004 |
| KR | 10-0588987 B1 | 6/2006 |
| WO | WO 2015/188182 A1 * | 12/2015 |

OTHER PUBLICATIONS

Kischkat et al: "Mid-infrared optical properties of thin films of aluminum oxide, titanium dioxide, silicon dioxide, aluminum nitride, and silicon nitride", Applied Optics, vol. 51, No. 38, Oct. 1, 2012, pp. 6789-6798, (10 pages total).

(Continued)

*Primary Examiner* — Hoa Pham (74) *Attorney, Agent, or Firm* — Sughrue Mion, PLLC (57) ABSTRACT

A method and apparatus for measuring a refractive index in a model-free manner are disclosed. The method includes: emitting a light to a surface plasmon generation layer that includes a nanoslot antenna and is disposed adjacent to a sample, to convert the light into surface plasmon; measuring a transmission of the sample from the light that is emitted onto the surface plasmon generation layer and passes through the sample; repeating the measuring the transmission while changing a length of the nanoslot antenna; and determining, based on a machine learning scheme, a restoration refractive index of the sample that is close to a graph of transmissions measured while changing the length of the nanoslot antenna from a library including a refractive index, a length of the nanoslot antenna, and a transmission at a specific wavelength.

20 Claims, 9 Drawing Sheets

(56) References Cited

U.S. PATENT DOCUMENTS

| | | | |
|---|---|---|---|
| 2012/0088229 A1 | | 4/2012 | Opitz et al. |
| 2015/0117015 A1* | | 4/2015 | Roh .................. H01L 33/02 |
| | | | 362/293 |
| 2018/0059505 A1* | | 3/2018 | Kyoung .................. G02F 1/292 |

OTHER PUBLICATIONS

Willets et al: "Localized Surface Plasmon Resonance Spectroscopy and Sensing", ANRV308-PC58-10, ARI, Oct. 19, 2006, pp. 267-297, (31 pages total).

Rodrigo et al: "Mid-infrared plasmonic biosensing with graphene", sciencemag.org, vol. 349, Issue 6244, Jul. 10, 2015, pp. 165-168, (5 pages total).

Beketov et al: "Surface plasmon resonance spectroscopy: prospects of superstrate refractive index variation for separate extraction of molecular layer parameters", Elsevier Science, Sensors and Actuators B, 1998, pp. 432-438, (7 pages total).

Kitamura et al: "Optical constants of silica glass from extreme ultraviolet to far infrared at near room temperature", Applied Optics, vol. 46, No. 33, Nov. 20, 2007, pp. 8118-8133, (16 pages total).

Choi et al: "Near-Zero Index: Optical Magnetic Mirror for Field Enhancement and Subwavelength Imaging Applications", Advanced Optical Materials, 2015, 3, pp. 1719-1725, (7 pages total).

Kang et al: "Substrate effect on aperture resonances in a thin metal film", Optics Express, vol. 17, No. 18, Aug. 31, 2009, pp. 15652-15658, (7 pages total).

Ju et al: "Graphene plasmonics for tunable terahertz metamaterials", Nature Nanotechnology, vol. 6, Oct. 2011, pp. 630-634, (5 pages total).

Fei et al: "Edge and Surface Plasmons in Graphene Nanoribbons", ACS Publications, Nano. Lett., 2015, 15, pp. 8271-8276, (6 pages total).

Tymchenko et al: "Faraday Rotation Due to Excitation of Magnetoplasmons in Graphene Microribbons", ACS Nano, vol. 7, No. 11, 2013, pp. 9780-9787, (8 pages total).

F. Javier Garcia De Abajo: "Graphene Plasmonics: Challenges and Opportunities", ACS Publications, 2014, 1, pp. 135-152, (18 pages total).

Gao et al: "Excitation of Plasmonic Waves in Graphene by Guided-Mode Resonances", ACS Nano, vol. 6, No. 9, 2012, pp. 7806-7813, (8 pages total).

Mikhailov et al: "New Electromagnetic Mode in Graphene", Physical Review Letters, Jul. 6, 2007, pp. 016803-1-016803-4, (4 pages total).

Stauber et al: "Optical conductivity of graphene in the visible region of the spectrum", Physical Review B 78, 085432, Aug. 26, 2008, pp. 085432-1-085432-8, (8 pages total).

Kyoung et al: "In situ measurement of graphene Fermi level by interband spectroscopy", Journal of Applied Physics 117, Jun. 12, 2015, pp. 223107-1-223107-6, (7 pages total).

* cited by examiner

METHOD AND APPARATUS FOR MEASURING REFRACTIVE INDEX IN MODEL-FREE MANNER

CROSS-REFERENCE TO RELATED APPLICATION

This application claims priority from Korean Patent Application No. 10-2016-0047561, filed on Apr. 19, 2016 in the Korean Intellectual Property Office, the disclosure of which is incorporated herein by reference in its entirety.

BACKGROUND

1. Field

Apparatuses and methods consistent with exemplary embodiments relate to measuring a refractive index in a model-free manner.

2. Description of the Related Art

For label-free detection of a certain material, a unique nature of the material (e.g., a refractive index) may be used.

Ellipsometry is usually used to measure a refractive index of a material. Ellipsometry is used to obtain information such as a refractive index and a thickness of a material by analyzing a polarization component of light returning after obliquely inputting linear polarization light to a sample. Since a Fresnel coefficient of light varies depending on a vertical or horizontal direction of an incident surface, polarization of light varies.

Since a beam has to be obliquely incident to a measurement sample to measure a refractive index by using ellipsometry, it is recommended that the measurement sample has a wide area. In addition, like a thin film, when a surface is clean and well defined, accurate measurement may be expected. Also, since a polarizer, a wavelength plate and the like besides an optical detector may be additionally installed and used for polarization analysis, these optical components may generate a measurement error if a visible wavelength band is not used.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide a method and apparatus for measuring a refractive index in a model-free manner, whereby a refractive index may be measured even for a sample having a small area and a completely unknown sample by using surface plasmon.

According to an aspect of an exemplary embodiment, there is provided a method of measuring a refractive index in a model-free manner including: emitting a light to a surface plasmon generation layer that includes a nanoslot antenna and is disposed adjacent to a sample, to convert the light into surface plasmon; measuring a transmission of the sample from the light that is emitted onto the surface plasmon generation layer and passes through the sample; repeating the measuring the transmission while changing a length of the nanoslot antenna; and determining, based on a machine learning scheme, a restoration refractive index of the sample that is close to a graph of transmissions measured while changing the length of the nanoslot antenna from a library including a refractive index, a length of the nanoslot antenna, and a transmission at a specific wavelength.

The library may be constructed while changing a wavelength of the emitted light within a range of interest.

Refractive indices for all the wavelengths within the range of interest may be obtained by repeating the measuring the transmission while changing the length of the nanoslot antenna and repeating the determining the restoration refractive index.

The library may be constructed by computing, for each nanoslot antenna length, a transmission at each point of a two-dimensional plane of an index set in which a real number value and an imaginary number value of an index are respectively a first coordinate value and a second coordinate value for the specific wavelength.

According to an aspect of another exemplary embodiment, there is provided an apparatus for measuring a refractive index in a model-free manner including: a transmission measurer using surface plasmon, comprising a surface plasmon generation layer that is disposed adjacent to a sample and a detector configured to detect a light transmitted through the surface plasmon generation layer; and a signal processor configured to obtain a refractive index measurement value of the sample by determining a restoration refractive index of the sample that is close to a transmission curve obtained from the detected light based on a library including a refractive index, a length of a nanoslot antenna, and a transmission at a specific wavelength.

The signal processor may be further configured to determine the restoration refractive index that is close to the transmission curve based on a machine learning scheme.

The apparatus may further include a memory configured to store the library.

The library may be constructed by computing, for each nanoslot antenna length, a transmission at each point of a two-dimensional plane of an index set in which a real number value and an imaginary number value of an index are respectively a first coordinate value and a second coordinate value for the specific wavelength.

The nanoslot antenna may be formed plural in number as an array on the surface plasmon generation layer.

The nanoslot antenna may be formed plural in number as a two-dimensional array on the surface plasmon generation layer.

The nanoslot antenna may have a width of about 10 nm to about 500 nm.

The nanoslot antenna may have a length of about 0.5 µm to about 15.5 µm.

When a width direction and a length direction of the nanoslot antenna are respectively a first direction and a second direction, the nanoslot antenna may be formed in a period of about 1.5 µm to about 4.5 µm along the first direction and formed in a period of about 0.5 µm to about 1.5 µm in addition to the length of the nanoslot antenna along the second direction.

The surface plasmon generation layer may include a metal or a metallic material, and the nanoslot antenna may have an intaglio or hole shape and may be disposed on the surface plasmon generation layer.

BRIEF DESCRIPTION OF THE DRAWINGS

The above and/or other aspects will be more apparent by describing certain exemplary embodiments, with reference to the accompanying drawings, in which.

DETAILED DESCRIPTION

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Figure 1:
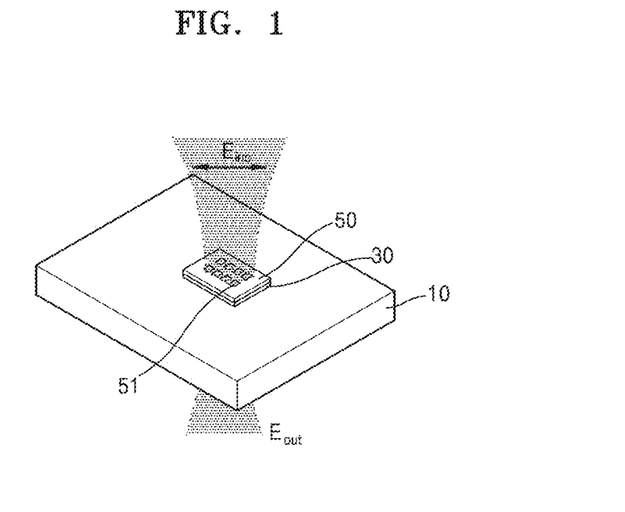
FIG. 1 is a conceptual diagram for describing a method of measuring a refractive index in a model-free manner by using surface plasmon, according to an exemplary embodiment.

FIG. 1 is a conceptual diagram for describing a method of measuring a refractive index in a model-free manner by using surface plasmon, according to an exemplary embodiment.

Referring to FIG. 1, to measure a refractive index of a sample 30 by using surface plasmon, a transmission is measured by emitting light on a measurement sample in which the sample 30 is placed closely to a surface plasmon generation layer 50. The transmission may be also referred to as transmittance. A nanoslot antenna 51 (e.g., an array of nanoslot antennas 51) may be formed on the surface plasmon generation layer 50. FIG. 1 illustrates a case in which a transmission is measured by emitting light $E_{inc}$ on the measurement sample having a stacked structure. The sample 30 is disposed on a substrate 10 and the surface plasmon generation layer 50 is disposed on the sample 30. The array of nanoslot antennas 51 is formed on the surface plasmon generation layer 50. The emitting light $E_{inc}$ is incident on the array of nanoslot antennas 51 and passes through the measurement sample to be emitted out as detecting light $E_{out}$.

Figure 2:
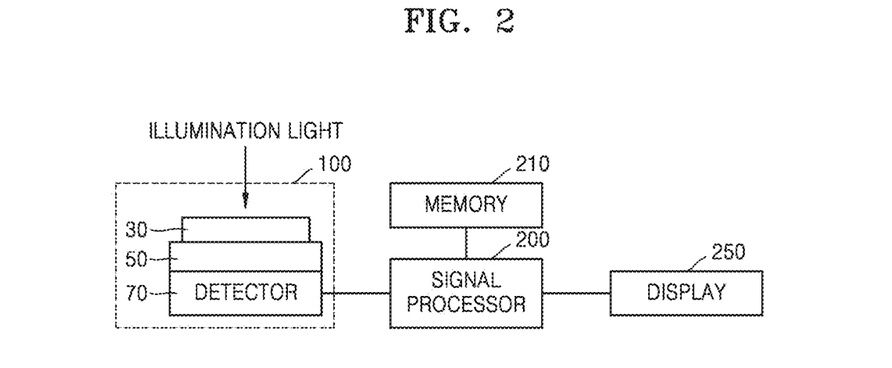
FIG. 2 is a block diagram of an apparatus for measuring a refractive index in a model-free manner by using surface plasmon, according to an exemplary embodiment.

FIG. 2 is a block diagram of an apparatus for measuring a refractive index in a model-free manner by using surface plasmon, according to an exemplary embodiment.

Referring to FIG. 2, the apparatus may include a transmission measurer 100 and a signal processor 200. The transmission measurer 100 is used to measure a transmission when illumination light is input from a light source. The transmission measurer 100 may be implemented by an optical sensor. The transmission measurer 100 may include the surface plasmon generation layer 50, to which the sample 30 is closely placed, and a detector 70 configured to detect light, which has transmitted through the surface plasmon generation layer 50. The light source is used to emit illumination light within a range of wavelength of interest and may be a wavelength-variable light source or include a plurality of light sources having different wavelengths, such that a refractive index is measurable all over wavelength within a range of interest. The signal processor 200 may obtain a measurement value of a refractive index of the sample 30 by finding out an index set for restoration close to a transmission curve, which is obtained from a detection signal of the detector 70, from a library constructed through computation so as to include an index, a length of the nanoslot antenna 51, and a transmission at a specific wavelength. The construction of the library will be described below.

According to an exemplary embodiment, the apparatus may further include a display 250 configured to display a processing result of the signal processor 200. In addition, according to an exemplary embodiment, the apparatus may further include a storage such as a memory 210 configured to store the constructed library. The library may be processed and constructed by the signal processor 200 and stored in the memory 210. As another example, the library may be constructed by a process of a separate device and stored in the memory 210, and the signal processor 200 of the apparatus according to an exemplary embodiment may operate and use the library stored in the memory 210.

FIG. 1 illustrates a case in which the sample 30 is between the substrate 10 and the surface plasmon generation layer 50, and FIG. 2 illustrates a case in which the sample 30 is disposed on the surface plasmon generation layer 50. The sample 30 may be on or beneath the surface plasmon generation layer 50 as long as the sample 30 is located closely to the surface plasmon generation layer 50 such that a refractive index of the sample 30 causes a change in the nature of localized surface plasmon generated by the surface plasmon generation layer 50.

In FIGS. 1 and 2, the surface plasmon generation layer 50 may include a metallic material or a metal. For example, the surface plasmon generation layer 50 may include a single metal, an alloy, graphene exhibiting metallicity, a two dimensional (2D) material, or the like. An array of a plurality of nanoslot antennas 51 configured to convert light emitted on the surface plasmon generation layer 50 into localized surface plasmon may be formed. The nanoslot antennas 51 may be formed in an intaglio or hole shape on the surface plasmon generation layer 50.

An effective size of the measurement sample may correspond to a size of the surface plasmon generation layer 50. The size of the measurement sample may be allowable for a wavelength of illumination light, e.g., wavelength/2 to infinity. For example, when light of a wavelength band (about 1 μm to about 16 μm) of a middle infrared (mid-IR) range is used as the illumination light, a measurement sample of a size of about 500 nm to an infinite size may be used. Therefore, measuring a refractive index, according to an exemplary embodiment, is not restricted to a size of a measurement sample. In addition, the measuring a refractive index, according to an exemplary embodiment, may apply light of a mid-IR range as the illumination light, and besides, a light source of various wavelength band may be applied according to types of the sample 30 to be measured.

Herein, since an existing refractive index measurement apparatus using ellipsometry, i.e., an ellipsometry equipment, requires that light is incident at an incident angle, a measurement sample of a wide area is needed. For example, for an ellipsometry equipment using light of a mid-IR range as illumination light, a measurement sample of a size of at least 10 mm×10 mm is needed to measure a refractive index.

However, according to the method and apparatus for measuring a refractive index, since localized surface plasmon is used and illumination light may be vertically incident to a measurement sample, a measurement sample of a small size may be applied, and a size of the measurement sample is not largely restricted. For example, when light of a mid-IR range is applied as illumination light, a measurement sample of a size of about 500 nm to an infinite size may be measured.

Figure 3:
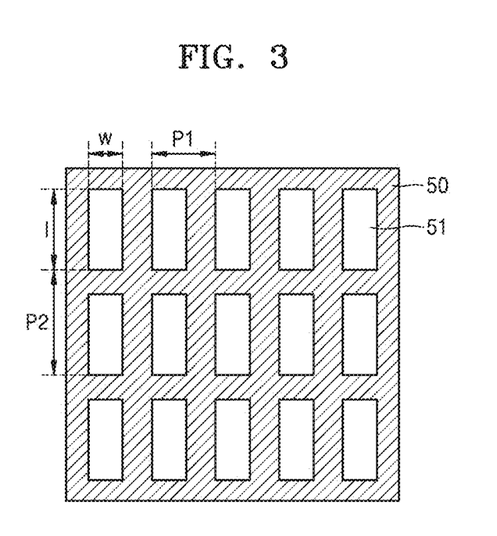
FIG. 3 illustrates an example of a two-dimensional (2D) array of nanoslot antennas formed on a surface plasmon generation layer.

On the surface plasmon generation layer 50, a 2D array of nanoslot antennas 51 may be formed, as shown in FIG. 3. FIG. 3 illustrates an example of a 2D array of nanoslot antennas 51 formed on the surface plasmon generation layer 50. An arrangement of the nanoslot antennas 51 formed on the surface plasmon generation layer 50 is not limited to FIG. 3 and may be variously modified.

Referring to FIG. 3, the nanoslot antenna 51 may have, for example, a width w of about 10 nm to about 500 nm and a length l of about 0.5 μm to about 15.5 μm. In addition, when a direction of the width w of the nanoslot antenna 51 is assumed as a first direction, and a direction of the length l of the nanoslot antenna 51 is assumed as a second direction, the nanoslot antennas 51 may formed in a period P1 of about 1.5 μm to about 4.5 μm along the first direction and formed in a period P2 of about 0.5 μm to about 1.5 μm in addition to the length l of the nanoslot antenna 51 along the second direction. Herein, the width w, the length l, the periods P1 and P2 of the nanoslot antenna 51 may vary according to a wavelength of light applied as illumination light.

The nanoslot antennas 51 formed on the surface plasmon generation layer 50 generate localized surface plasmon. The surface plasmon is vibration of charges collected from a surface of a metal. When a specific molecule exists, a refractive index of a point close to a nanostructure having metallicity changes, thereby inducing a sharp change and deformation of surface plasmon resonance (SPR). This SPR involves information about an optical constant of a nearby material.

According to the method of measuring a refractive index, the nature of localized surface plasmon generated by the nanoslot antennas 51 of the surface plasmon generation layer 50 varies according to a refractive index of the sample 30 close to the surface plasmon generation layer 50 including a metal or a metallic material, the change in the nature of the localized surface plasmon is detected as a change in a transmission, and a complex refractive index of the sample 30 is extracted through a machine learning algorithm based on this detection signal.

A refractive index may be measured through a process described below.

Once light is emitted onto the surface plasmon generation layer 50 which is disposed adjacent to the sample 30, the detector 70 measures a transmission of the sample 30. The operation of measuring a transmission by illuminating light on the surface plasmon generation layer 50, to which the sample 30 is located closely, while changing a length of the nanoslot antenna 51 is repeated.

Separately from the transmission measurement, a library is constructed through computation such that the library includes a refractive index, a length of the nanoslot antenna 51, and a transmission of a sample 30 at a specific wavelength. The library is constructed by computing a transmission while changing each set of refractive indices having, for example, a real part of 0.01 to 3.4 and an imaginary part of 0 to 3.4 for only a material portion to be measured under conditions such as a measurement sample and a measurement environment. An index set for restoration close to a graph of transmissions measured through experiments while changing a length of the nanoslot antenna 51 is found from the constructed library by a machine learning scheme. This value may be an index value of the material at the specific wavelength.

As described above, the library may be constructed while changing a specific wavelength all over wavelengths within a range of interest. The library constructed as described above is a 4D library of the wavelength, index, length of the nanoslot antenna 51, and transmission. The 4D library may be constructed in advance, and the constructed 4D library may be stored in a storage such as the memory 210 and used to extract a refractive index by using a machine learning algorithm or the like during a refractive index measurement process.

A refractive index of the sample 30 is extracted by determining, by a machine learning scheme, an index set for restoration close to a transmission graph measured while changing a length of the nanoslot antenna 51 from the 4D library constructed through computation such that the 4D library includes an index, a length of the nanoslot antenna 51, and a transmission at a specific wavelength.

The 4D library may be constructed while changing a specific wavelength all over wavelengths within a range of interest. In addition, refractive indices all over the wavelengths within the range of interest may be obtained by repeating an operation of measuring a transmission by emitting light on the surface plasmon generation layer 50, to which the sample 30 is located closely for each length of the nanoslot antenna 51, while changing a specific wavelength all over the wavelengths within the range of interest and repeating an operation of determining, by a machine learning scheme, an index set for restoration close to a measured transmission graph from the 4D library.

According to the method and apparatus for measuring a refractive index, a refractive index may be measured using characteristics of surface plasmon without any mathematical model or angle spectrum.

Figure 4A:
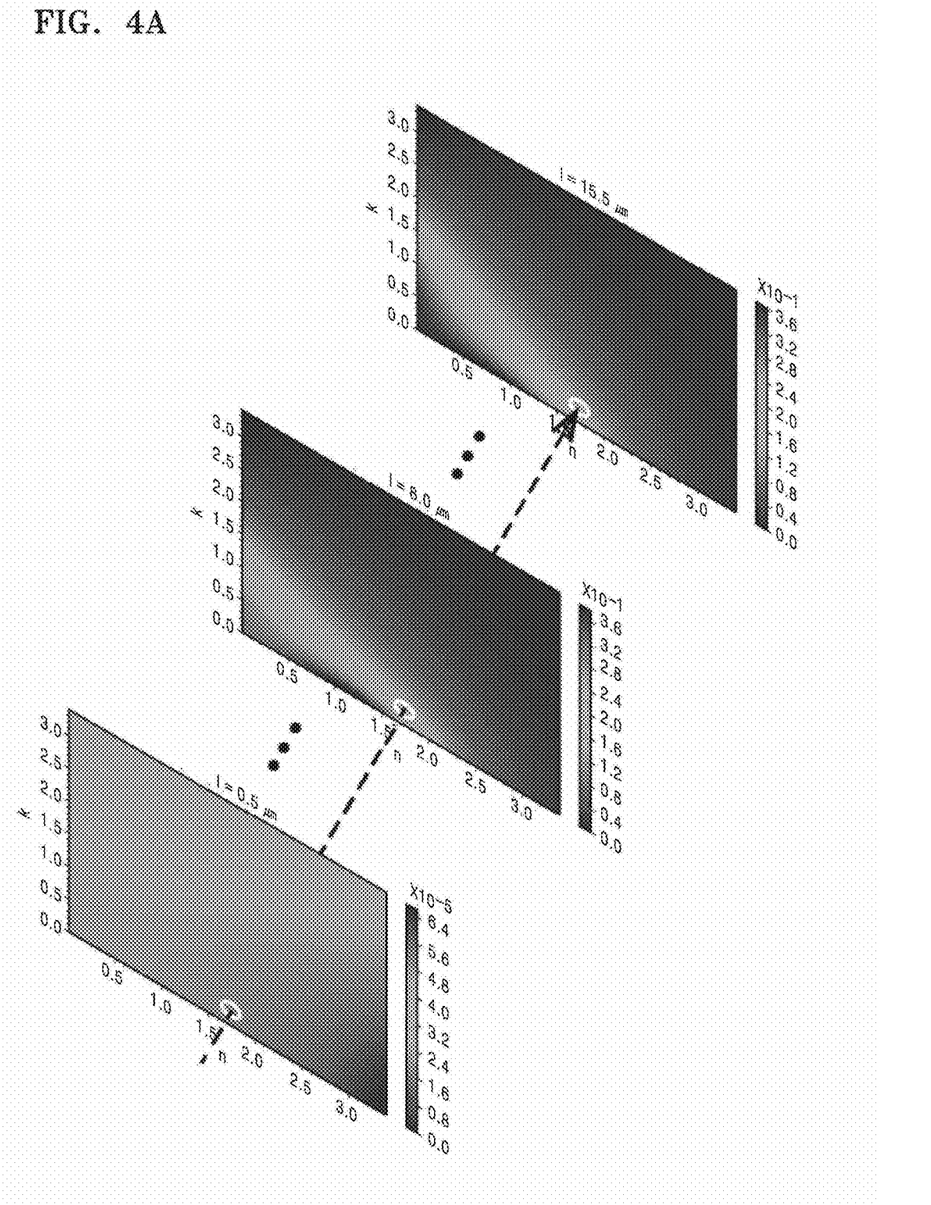
FIG. 4A illustrates a four-dimensional (4D) library including a real part value and an imaginary part value of a refractive index, a length of a nanoslot antenna, and a transmission at a specific wavelength.
Figure 4B:
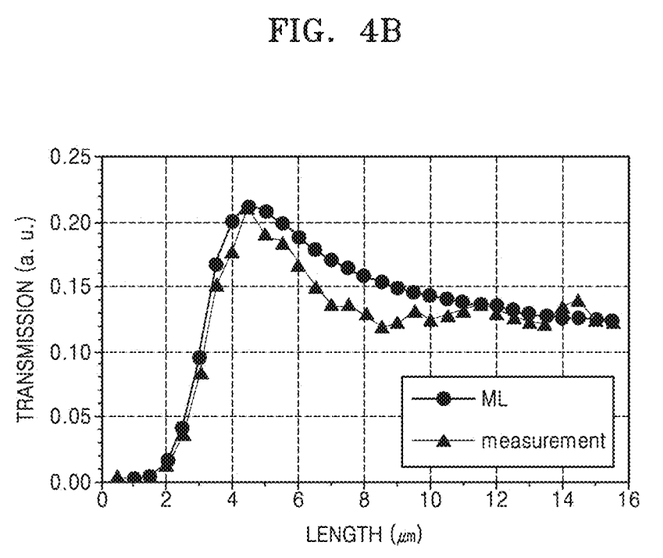
FIG. 4B illustrates a graph of values obtained by measuring a change in a transmission according to a length of a nanoslot antenna at a specific wavelength and a comparative graph of a result when an optimal index is obtained using a machine learning scheme.

FIG. 4A illustrates a 4D library including a real part value and an imaginary part value of a refractive index, a length of the nanoslot antenna 51, and a transmission at a specific wavelength. FIG. 4B illustrates a graph of values obtained by measuring a change in a transmission according to a length of the nanoslot antenna 51 at the specific wavelength and a comparative graph of a result when an optimal index is obtained using a machine learning scheme. In FIG. 4B, the x axis indicates a length of the nanoslot antenna 51, and the y axis indicates a transmission. "Measurement" indicates a measured value of a change in a transmission of a measurement sample according to a length of the nanoslot antenna 51, and "ML" indicates a change in a transmission when an optimal index is found using the machine learning scheme according to a length of the nanoslot antenna 51.

A result of FIG. 4B is obtained by preparing 31 types of measurement samples as shown in FIG. 1, including a periodic array of nanoslot antennas 51 such that various kinds of SPR occurs. A test is designed such that all the measurement samples have an x-axis period P1 of about 3.5 μm, a total area is commonly 100 μm×100 μm, the length l of the nanoslot antenna 51 varies within a range of 0.5 μm to 15.5 μm, and a y-axis period P2 is longer by about 0.5 μm than the length l. A width of each nanoslot antenna 51 is about 500 nm. A strong interaction between the surface plasmon generation layer 50 and the sample 30 close thereto may be shown as a unique transmission curve form measurable by an existing Fourier transform infrared (FT-IR) device with respect to geometric normal incidence. A polarization direction of illumination light may be perpendicular to a long axis of the nanoslot antenna 51. A transmission as a function of a length of the nanoslot antenna 51 may be measured as shown in FIG. 4B at a wavenumber of 760 $cm^{-1}$. The transmission rapidly increases up to 0.22 and then gradually decreases when the length of the nanoslot antenna 51 is about 4.5 μm. Eventually, the transmission is saturated for nanoslot antennas 51 of a length longer than about 8.0 μm. This asymptotic behavior may be easily understood since a very long nanoslot antenna 51 may be considered as a nanoslit. To obtain the measurement result of FIG. 4B, for example, the measurement sample of FIG. 1 may be formed in a stacked structure of a silicon substrate 10, a $SiO_2$ layer (the sample 30), and the surface plasmon generation layer 50 including gold (Au) thereon.

To extract an optical parameter from the transmission curve obtained through measurements, a 4D library including a transmission, a complex refractive index (n+ik, n and k are real numbers), and a length of the nanoslot antenna 51 may be constructed as shown in FIG. 4A through analysis computation. In FIG. 4A, each 3D contour plot indicates a complex refractive index versus a transmission when a nanoslot antenna 51 of a specific length is applied. FIG. 4A illustratively shows only contour plots of three cases in which the length l of the nanoslot antenna 51 is 0.5, 8.0, and 15.5 μm because of a restricted space.

A geodesic line closest to the measurement data in FIG. 4B is found from the constructed library including a transmission, a complex refractive index (n+ik, n and k are real numbers), and a length of the nanoslot antenna 51. In FIG. 4A, the geodesic line closest to the measurement data in FIG. 4B is represented with an arrow penetrating through the three contour plots.

To do this job, a machine learning algorithm (e.g., a K-nearest neighbors (K-NN) algorithm) may be used. The K-NN algorithm is one of the machine learning algorithms. The K-NN algorithm is a non-parametric method widely used to solve a classification or regression problem. In K-NN regression, an input is configured with K nearest training examples to each query point, wherein K denotes a positive integer value designated by a user, and an output is an attribute value of an object. Since a fundamental K-NN algorithm for regression uses uniform weights, each point within localized neighbors uniformly contributes to regression of a query point.

According to the present exemplary embodiment, in a machine learning operation, an input of a training set is a calculated transmission depending on a length of the nanoslot antenna 51, and an output is a real part and an imaginary part of a refractive index. After performing a machine learning using all 4D libraries, a complex refractive index of the measurement data may be predicted as shown in the graph marked with triangles in FIG. 4B. At a wavenumber of 760 $cm^{-1}$, when the number of nearest neighbors is 5 (K=5) in a uniform weight option, a result of machine learning was 1.74+0.24i. The result of machine learning does not exhibit a significant difference according to a value of K or a weight option, and since computation was performed every 0.1 for n and k, the transmission curve of 1.74+0.24i is not included in a 4D library. An effective number extends to at least two decimal places, and this may be a significant point of a machine learning algorithm which may provide a solution over given data, which is discriminated from an existing least square method. Transmissions computed based on the predicted refractive index 1.74+0.24i are marked with circles in FIG. 4B. As known from comparison between the measured values and the computed values in FIG. 4B, the measured values and the computed values indicate that a complex refractive index may be extracted by the method and apparatus using surface plasmon according to the present exemplary embodiment.

A refractive index of a 300 nm-thickness $SiO_2$ thin film grown by thermal chemical vapor deposition (CVD) is well known, and particularly, since the refractive index dramatically varies due to strong phonon absorption in a mid-IR range, the 300 nm-thickness $SiO_2$ thin film is used to verify that a refractive index is measurable by the method and apparatus for measuring a refractive index, according to the present exemplary embodiment.

Figure 5A:
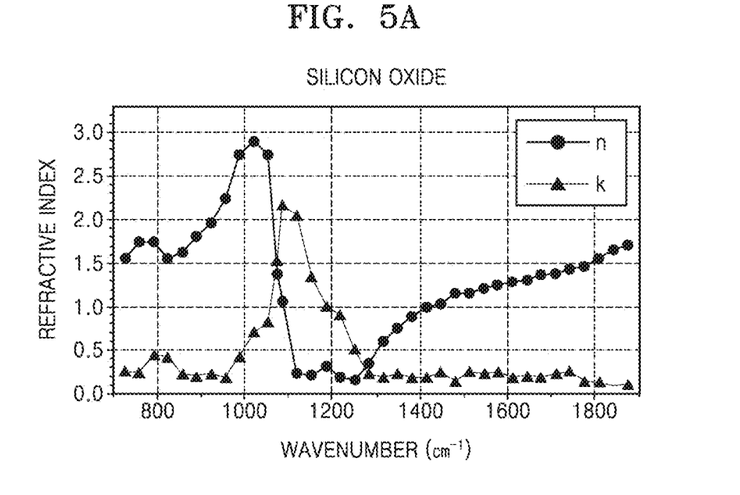
FIG. 5A illustrates a result of obtaining a complex refractive index of a silicon oxide ($SiO_2$) thin film of a thickness of about 300 nm by applying the method of measuring a refractive index, according to an exemplary embodiment.
Figure 5B:
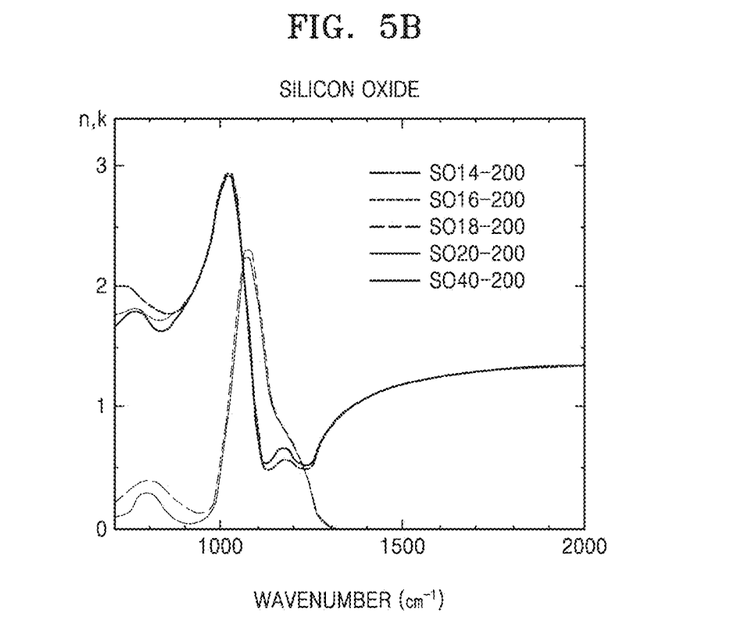
FIG. 5B illustrates, as a comparative example, a refractive index of the $SiO_2$ thin film, which is extracted using a commercial ellipsometry equipment.
Figure 5C:
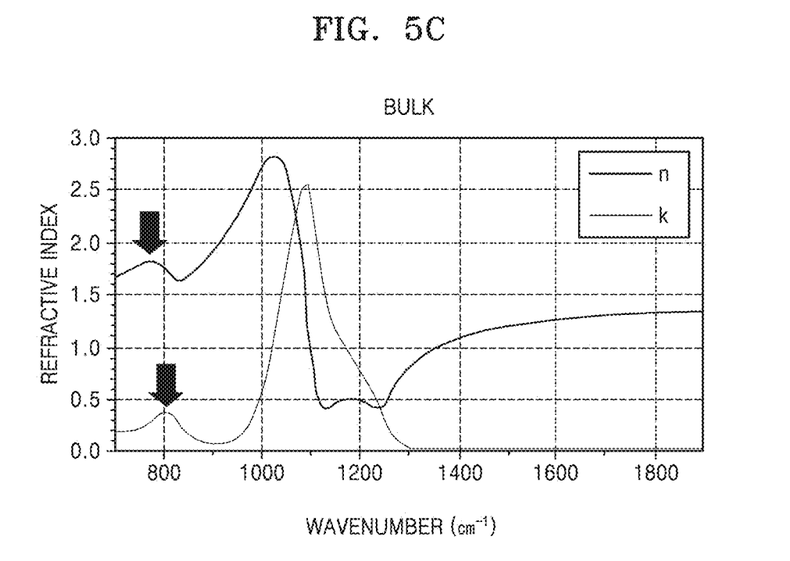
FIG. 5C illustrates a refractive index of a bulk $SiO_2$ material applied as a criterion.

FIG. 5A illustrates a result of obtaining a complex refractive index of a $SiO_2$ thin film of a thickness of about 300 nm by applying the method of measuring a refractive index, according to an exemplary embodiment. FIG. 5B illustrates, as a comparative example, a refractive index of the $SiO_2$ thin film, which is extracted using a commercial ellipsometry equipment. FIG. 5C illustrates a refractive index of a bulk $SiO_2$ material applied as a criterion. In FIGS. 5A, 5B, and 5C, graphs indicated with n show a real part value of a refractive index, and graphs indicated with k show an imaginary part value of the refractive index.

FIG. 5A shows a refractive index dispersion curve of $SiO_2$, which is obtained by selecting 40 or more almost equally-spaced wavenumbers in a wavenumber range of 700 $cm^{-1}$ to 1900 $cm^{-1}$ and applying the method and apparatus for measuring a refractive index, according to the present embodiment, to each point. In FIG. 5A, in real part (n) and imaginary part (k) graphs of a refractive index, points marked with circles and triangles correspond to values obtained with respect to each sample.

As shown in FIG. 5A, even when the method and apparatus for measuring a refractive index are applied according to the present exemplary embodiment, abnormal dispersion (1,020 to 1,250 cm$^{-1}$) associated with a wavenumber and reduction of n and strong resonance absorption associated with horizontal optical phonon (1,088 cm$^{-1}$) of the SiO$_2$ thin film are observed. This dispersion characteristic curve is a unique fingerprint of a SiO$_2$ material.

As shown in FIG. 5A, a refractive index may be extracted by applying the method and apparatus for measuring a refractive index by using surface plasmon, according to the present embodiment, without using any of a mathematical dielectric model and an angle spectroscope to obtain an entire refractive curve.

Comparing FIG. 5A with FIG. 5C, when the present exemplary embodiment is applied, even a small localized change in a dispersion curve, which is very similar to that of the bulk SiO$_2$ material applied as a criterion, may be obtained. However, comparing FIG. 5B with FIG. 5C, when ellipsometry is applied, a small localized change in a dispersion curve cannot be described. Therefore, the method of measuring a refractive index, according to an exemplary embodiment, may extract an optical parameter of a thin film more sensitive than existing ellipsometry.

Figure 6A:
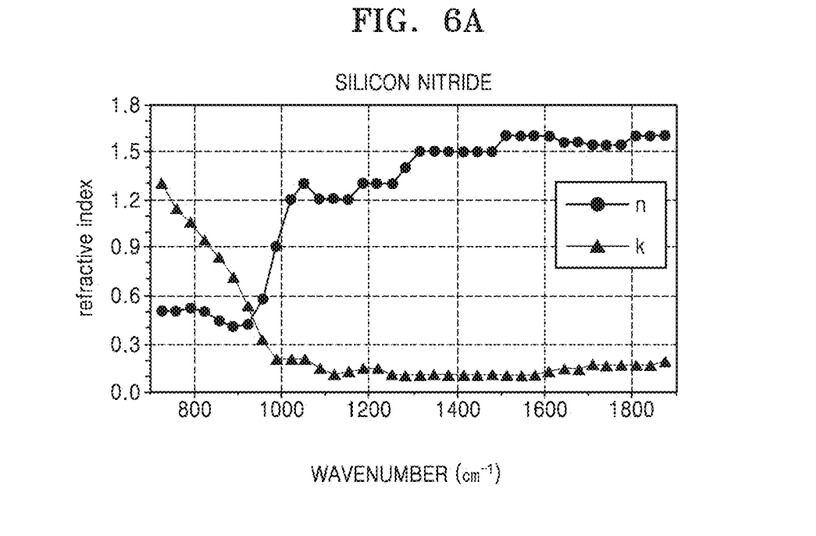
FIG. 6A illustrates a result of obtaining a complex refractive index of a silicon nitride (SiN) thin film of a thickness of about 300 nm by applying the method of measuring a refractive index, according to an exemplary embodiment.
Figure 6B:
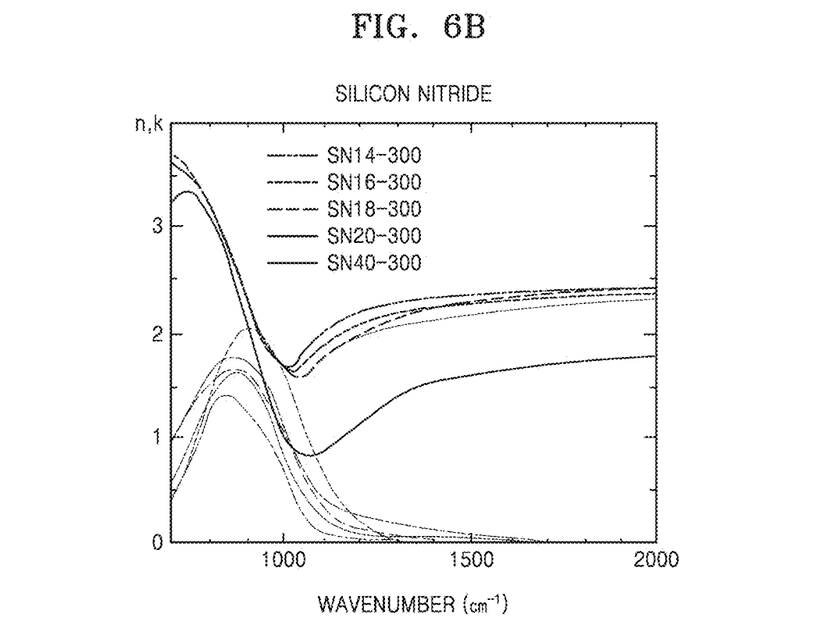
FIG. 6B illustrates, as a comparative example, a refractive index of the SiN thin film, which is extracted using the commercial ellipsometry equipment.

As another example, FIG. 6A illustrates a result of obtaining a complex refractive index of a silicon nitride (SiN) thin film of a thickness of about 300 nm by applying the method of measuring a refractive index, according to an exemplary embodiment. FIG. 6B illustrates, as a comparative example, a refractive index of the SiN thin film, which is extracted using the commercial ellipsometry equipment. In FIGS. 6A and 6B, a graph indicated with n shows a real part value of a refractive index, and a graph indicated with k shows an imaginary part value of the refractive index.

Figure 7A:
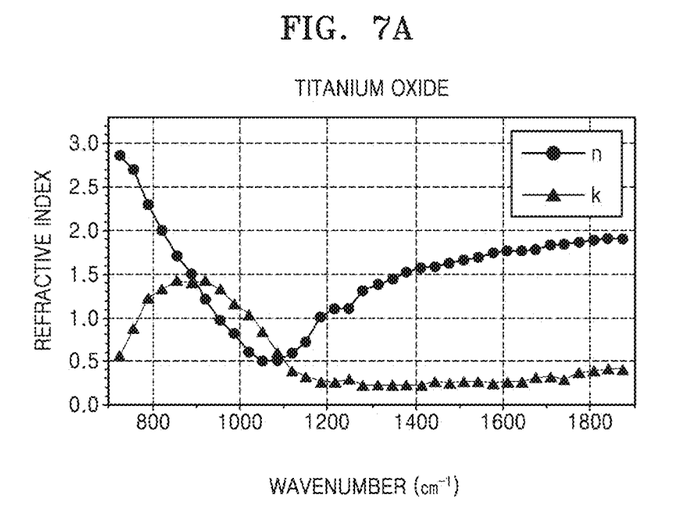
FIG. 7A illustrates a result of obtaining a complex refractive index of a titanium oxide ($TiO_2$) thin film of a thickness of about 300 nm by applying the method of measuring a refractive index, according to an exemplary embodiment.
Figure 7B:
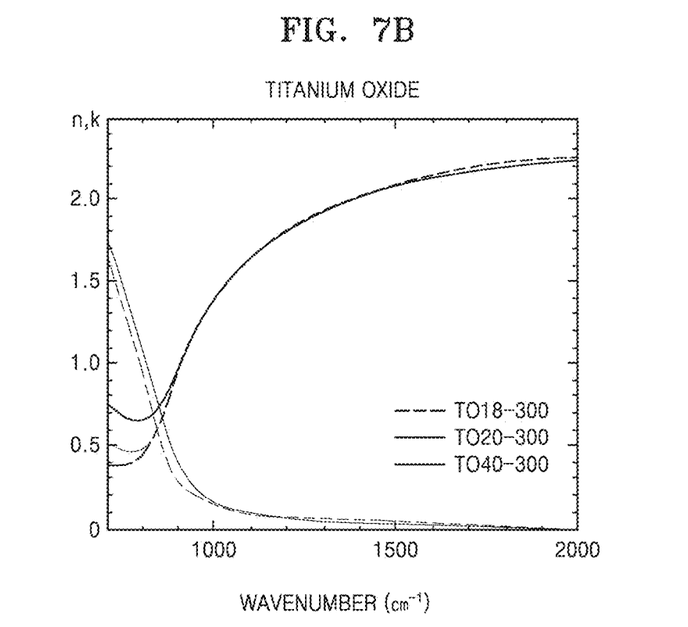
FIG. 7B illustrates, as a comparative example, a refractive index of the $TiO_2$ thin film, which is extracted using the commercial ellipsometry equipment.

As another example, FIG. 7A illustrates a result of obtaining a complex refractive index of a titanium oxide (TiO$_2$) thin film of a thickness of about 300 nm by applying the method of measuring a refractive index, according to an exemplary embodiment. FIG. 7B illustrates, as a comparative example, a refractive index of the TiO$_2$ thin film, which is extracted using the commercial ellipsometry equipment. In FIGS. 7A and 7B, a graph indicated with n shows a real part value of a refractive index, and a graph indicated with k shows an imaginary part value of the refractive index.

Figure 8A:
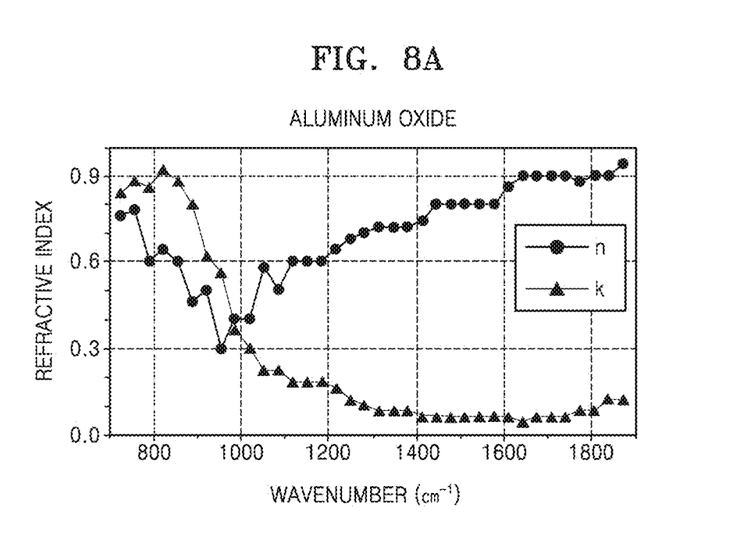
FIG. 8A illustrates a result of obtaining a complex refractive index of an aluminum oxide ($Al_2O_3$) thin film of a thickness of about 42 nm by applying the method of measuring a refractive index, according to an exemplary embodiment.
Figure 8B:
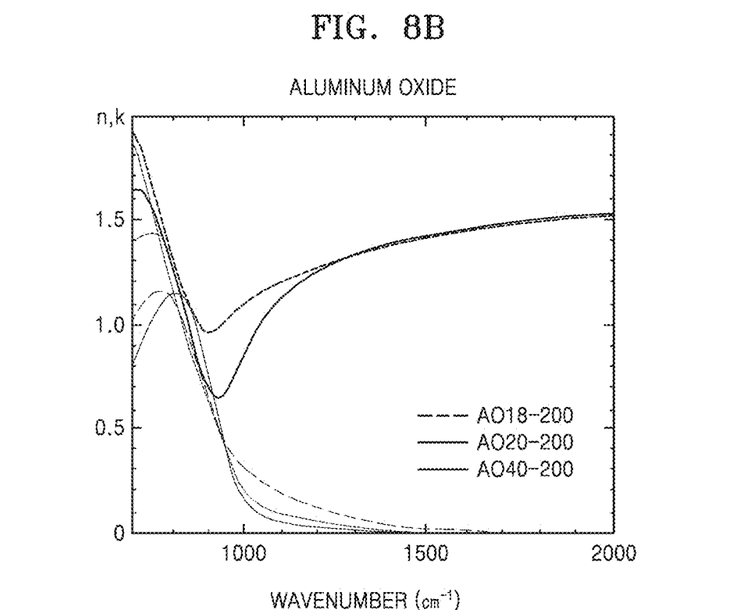
FIG. 8B illustrates, as a comparative example, a refractive index of the $Al_2O_3$ thin film, which is extracted using the commercial ellipsometry equipment.

As another example, FIG. 8A illustrates a result of obtaining a complex refractive index of an aluminum oxide (Al$_2$O$_3$) thin film of a thickness of about 42 nm by applying the method of measuring a refractive index, according to an exemplary embodiment. FIG. 8B illustrates, as a comparative example, a refractive index of the Al$_2$O$_3$ thin film, which is extracted using the commercial ellipsometry equipment. In FIGS. 8A and 8B, a graph indicated with n shows a real part value of a refractive index, and a graph indicated with k shows an imaginary part value of the refractive index.

As known from the comparison between FIGS. 6A and 6B, the comparison between FIGS. 7A and 7B, and the comparison between FIGS. 8A and 8B, the refractive indices of SiN, TiO$_2$, and Al$_2$O$_3$, which are obtained by applying the method and apparatus for measuring a refractive index, according to one or more exemplary embodiments, match the result described above.

Herein, the graphs of FIGS. 5B, 6B, 7B, and 8B are reported in Applied optics, Vol. 51, No. 28, "Mid-infrared optical properties of thin films of aluminum oxide, titanium dioxide, silicon dioxide, aluminum nitride, and silicon nitride" (Oct. 1, 2012).

As described above, when the method and apparatus for measuring a refractive index, according to the present exemplary embodiment, are applied, refractive indices of various types of target materials may be measured in a model-free manner without using a mathematical model. In addition, since a 4D library constructed once does not depend on a type of a target material, when a thickness of a thin film and a nanoantenna structure with respect to a transmission curve match 4D library conditions, the 4D library may be repetitively used for any material.

As described above, complex refractive indices of various types of samples 30 may be measured in a technically significant mid-IR range by the method and apparatus for measuring a refractive index by using surface plasmon. To this end, a measurement process may include three stages as below. First, a transmission characteristic curve determined by strong bonding between various surface plasmon modes and an ambient medium is measured. Second, a 4D library including a transmission as a function of parameters such as a refractive index and a length of the nanoslot antenna 51 is constructed through computation. Third, a complex refractive index is extracted from the 4D library by using a machine learning algorithm with respect to the measured transmission characteristic curve.

According to the method and apparatus for measuring a refractive index, according to the present exemplary embodiment, besides the above-described process, any of a dielectric model and angle spectrophotometry is not necessary. Therefore, the method and apparatus for measuring a refractive index, according to the present embodiment, may be used to check not only a mathematical dielectric mode but also a Kramers-Kronig relationship in the future. In addition, compared with existing ellipsometry, a very small-sized measurement sample may be measured because of subwavelength-scale optical confinement by surface plasmon, and thus, the method and apparatus for measuring a refractive index, according to the present embodiment, may be applied to label-free detection of a biomolecule included in optical characteristics of a random-shaped droplet or a small 2D material, and the like.

Although a case in which a machine learning algorithm is applied to the method and apparatus for measuring a refractive index in a model-free manner, according to one or more exemplary embodiments, various algorithms besides the machine learning algorithm may be applied, to extract a refractive index, to the method and apparatus for measuring a refractive index in a model-free manner, according to one or more exemplary embodiments.

According to the method and apparatus for measuring a refractive index, according to one or more exemplary embodiments, a refractive index of even a sample of a small area may be measured using surface plasmon. In addition, since a transmission of a measurement sample in which a sample is placed closely to a surface plasmon generation layer is measured, and an index set for restoration close to a transmission curve may be obtained using an algorithm, a refractive index of a completely unknown sample may also be measured in a model-free manner in which a mathematical mode is not used. In addition, since illumination light does not have to be incident at a certain angle, the apparatus may be simply set up.

The foregoing exemplary embodiments are merely exemplary and are not to be construed as limiting. The present teaching can be readily applied to other types of apparatuses.

Also, the description of the exemplary embodiments is intended to be illustrative, and not to limit the scope of the claims, and many alternatives, modifications, and variations will be apparent to those skilled in the art.

What is claimed is:

1. A method of measuring a refractive index in a model-free manner, the method comprising:
   emitting a light to a surface plasmon generation layer that includes a nanoslot antenna and is disposed adjacent to a sample, to convert the light into surface plasmon;
   measuring a transmission of the sample from the light that is emitted onto the surface plasmon generation layer and passes through the sample;
   repeating the measuring the transmission while changing a length of the nanoslot antenna; and
   determining, based on a machine learning scheme, a restoration refractive index of the sample that is close to a graph of transmissions measured while changing the length of the nanoslot antenna from a library including a refractive index, a length of the nanoslot antenna, and a transmission at a specific wavelength.

2. The method of claim 1, wherein the library is constructed while changing a wavelength of the emitted light within a range of interest.

3. The method of claim 2, wherein refractive indices for all the wavelengths within the range of interest are obtained by repeating the measuring the transmission while changing the length of the nanoslot antenna and repeating the determining the restoration refractive index.

4. The method of claim 1, wherein the library is constructed by computing, for each nanoslot antenna length, a transmission at each point of a two-dimensional plane of an index set in which a real number value and an imaginary number value of an index are respectively a first coordinate value and a second coordinate value for the specific wavelength.

5. The method of claim 1, wherein the nanoslot antenna is formed plural in number as an array on the surface plasmon generation layer.

6. The method of claim 5, wherein the nanoslot antenna is formed plural in number as a two-dimensional array on the surface plasmon generation layer.

7. The method of claim 6, wherein the nanoslot antenna has a width of about 10 nm to about 500 nm.

8. The method of claim 7, wherein the nanoslot antenna has a length of about 0.5 μm to about 15.5 μm.

9. The method of claim 7, wherein, when a width direction and a length direction of the nanoslot antenna are respectively a first direction and a second direction, the nanoslot antenna is formed in a period of about 1.5 μm to about 4.5 μm along the first direction and formed in a period of about 0.5 μm to about 1.5 μm in addition to the length of the nanoslot antenna along the second direction.

10. The method of claim 1, wherein the surface plasmon generation layer comprises a metal or a metallic material, and
    the nanoslot antenna has an intaglio or hole shape and is disposed on the surface plasmon generation layer.

11. An apparatus for measuring a refractive index in a model-free manner, the apparatus comprising:
    a transmission measurer using surface plasmon, comprising a surface plasmon generation layer that is disposed adjacent to a sample and a detector configured to detect a light transmitted through the surface plasmon generation layer; and
    a signal processor configured to obtain a refractive index measurement value of the sample by determining a restoration refractive index of the sample that is close to a transmission curve obtained from the detected light based on a library including a refractive index, a length of a nanoslot antenna, and a transmission at a specific wavelength.

12. The apparatus of claim 11, wherein the signal processor is further configured to determine the restoration refractive index that is close to the transmission curve based on a machine learning scheme.

13. The apparatus of claim 11, further comprising a memory configured to store the library.

14. The apparatus of claim 11, wherein the library is constructed by computing, for each nanoslot antenna length, a transmission at each point of a two-dimensional plane of an index set in which a real number value and an imaginary number value of an index are respectively a first coordinate value and a second coordinate value for the specific wavelength.

15. The apparatus of claim 11, wherein the nanoslot antenna is formed plural in number as an array on the surface plasmon generation layer.

16. The apparatus of claim 15, wherein the nanoslot antenna is formed plural in number as a two-dimensional array on the surface plasmon generation layer.

17. The apparatus of claim 16, wherein the nanoslot antenna has a width of about 10 nm to about 500 nm.

18. The apparatus of claim 17, wherein the nanoslot antenna has a length of about 0.5 μm to about 15.5 μm.

19. The apparatus of claim 17, wherein, when a width direction and a length direction of the nanoslot antenna are respectively a first direction and a second direction, the nanoslot antenna is formed in a period of about 1.5 μm to about 4.5 μm along the first direction and formed in a period of about 0.5 μm to about 1.5 μm in addition to the length of the nanoslot antenna along the second direction.

20. The apparatus of claim 11, wherein the surface plasmon generation layer comprises a metal or a metallic material, and
    the nanoslot antenna has an intaglio or hole shape and is disposed on the surface plasmon generation layer.

* * * * *